United States Patent [19]
Repine et al.

[11] Patent Number: 5,596,011
[45] Date of Patent: Jan. 21, 1997

[54] METHOD FOR THE TREATMENT OF MACULAR DEGENERATION

[76] Inventors: Karen M. Repine; John E. Repine, both of 2275 Cherry Hills Farm Dr., Englewood, Colo. 80110

[21] Appl. No.: 418,645

[22] Filed: Apr. 6, 1995

[51] Int. Cl.$^6$ .................... A61K 31/425; A61K 31/195; A61K 31/13
[52] U.S. Cl. .................... 514/369; 514/562; 514/665; 514/912
[58] Field of Search .................... 514/369, 562, 514/665, 912

[56] References Cited

PUBLICATIONS

S. H. Sarks, John P. Sarks, Age–Related Macular Degeneration: Atrophic Form, vol. Two, Macular Disease, Chapter 64, 1989, pp. 149–173.
S. West et al., Are Antioxidants or Supplements Protective for Age–Related Macular Degeneration?, Archives of Ophthalmology, Feb. 1994, pp. 222–227.
M. M. E. Bridgeman et al., Cysteine and Glutathione Concentrations in Plasma and Bronchoalveolar Lavage Fluid (1991) after Treatment with N–Acetylcysteine, Dept. of Biochemistry, U. of Edinburgh, Medical School, pp. 39–42.
M. M. E. Bridgeman, et al., Effect of N–Acetyl Cysteine on the Concentrations of Thiols in Plasma, Bronchoalveolar Lavage Fluid, and Lung Tissue, Dept. of Biochemistry, U. of Edinburgh Med. School, 1994, pp. 670–675.
B. de Quay et al., Glutathione Depletion in HIV–Infected Patients: Role of Cysteine Deficiency and Effect of Oral N–Acetylcysteine, Current Science Ltd., 1992, pp. 875–876.
Wayne E. Fung, Interferon Alpha 2a for Treatment of Age–Related Macular Degeneration, American Jounal of Ophthalmology, Sep. 1991, pp. 349–350.

W. de Backer, Inflammatory Mediators in Acute Lung Injury and Copd: Effects of N–Acetylcysteine, Pulmo script, Sep. 1994.
G. R. Bernard, N–Acetylcysteine in Experimental and Clinical Acute Lung Injury, The American Journal of Medicine, Sep. 1991.
O. I. Aruoma et al., The Antioxidant Action of N–Acetylcysteine: Its Reaction with Hydrogen Peroxide, Hydroxyl Radical, Superoxide, and Hypochlorous Acid, Free Radical Biology & Medicine, 1989, pp. 593–597.
I. H. Chisholm, The Prospects for New Treatments in Age–Related Macular Degeneration, British Journal of Ophthalmology, 1993.
P. Ko et al, Understanding Macular Degeneration, Hospital Medicine, Sep. 1994, pp. 47–55.
J. M. Seddon et al, Vitamins, Minerals, and Macular Degeneration, Archives of Ophthalmology, 1994, pp. 176–179.

Primary Examiner—Zohreh Fay

[57] ABSTRACT

Macular degeneration is an age-related eye disease for which there is no known treatment to date that has been shown to be effective at treating or preventing the onset or progression of the disease. Current treatment of non-exudative (dry form) macular degeneration is limited to early diagnosis and careful followup, while symptomatic treatment of exudative (wet form) macular degeneration includes laser photocoagulation therapy, surgery, low dose radiation (teletherapy), and anti-oxidant or anti-inflammatory therapies. The present invention relates to a new method for treating or preventing the onset or progression of macular degeneration, comprising periodic administration of a glutathione (GSH) enhancing agent alone or in conjunction with at least one of an anti-oxidant or an anti-inflammatory therapy, and possibly in addition to one or more of the symptomatic treatments mentioned above.

14 Claims, 3 Drawing Sheets

METHOD FOR THE TREATMENT OF MACULAR DEGENERATION

BACKGROUND OF THE INVENTION

1. Field of the Invention

The present invention relates to a new method for treating or preventing the onset or progression of macular degeneration. More particularly, the invention relates to a new method of treatment which comprises periodic administration of a dosage of glutathione (GSH) enhancing agent alone or in conjunction with other treatments such as anti-oxidant or anti-inflammatory therapy or perhaps commonly known symptomatic treatments.

2. Description of Related Art

Macular degeneration is an age-related eye disease for which there is no known treatment to date that has been shown to be effective at treating or preventing the onset or progression of the disease. Macular degeneration is the leading cause of new blindness in aging individuals, particularly individuals over 65 years of age.

Macular degeneration is a single disorder which is often characterized as one of two types, non-exudative (dry form) or exudative (wet form). Although both types are bilateral and progressive, each type may reflect different pathological processes. An example of a reference which provides a general background for the understanding, identification, and illustration of limited treatments of macular degeneration is Ko, P. and Wong, S., *Understanding Macular Degeneration, Hospital Medicine* 47–55 (September 1994).

Both exudative (wet form) and non-exudative (dry form) macular degeneration are typically accompanied by the formation of drusen. Drusen are characterized by irregular, discrete, round yellow-white deposits which accumulate in the retina (back of the eye) between the basement membrane of the retinal pigment epithelium (RPE) and the rest of Bruch's membrane. The presence of drusen most likely reflect abnormalities in retinal pigment epithelial function. Drusen deposits can be further categorized into hard drusen or soft drusen. Hard or nodular drusen derive from debris accumulation from retinal pigment epithelial cells in Bruch's membrane. Soft drusen are usually larger than hard drusen and have soft, indistinct margins. Soft drusen are small detachments of the retinal pigment epithelium and presumably derive from diffuse retinal pigment epithelial dysfunction. Soft drusen can also derive from diffuse or confluent drusen, which further derive from a thickening of the inner portion of Bruch's membrane. Calcified drusen are characterized by a glistening appearance and are the consequence of calcification of nodular and diffuse drusen formations.

Non-exudative (dry form) macular degeneration involves atrophy and degeneration of the outer retina, retinal pigment epithelium, Bruch's membrane, and choriocapillaris. The resultant effects of non-exudative macular degeneration are formation of drusen, pigmentary changes, and atrophy. Dysfunction of the retinal pigment epithelium, in particular, leads to the loss of photoreceptors, which are metabolically dependent on the retinal pigment epithelium.

Exudative (wet form) macular degeneration is characterized by serous or hemorrhagic separation of the retinal pigment epithelium or neurosensory layer. Patients may develop choroidal neovascularization, which is manifested as fluid accumulation, hemorrhage, and/or lipid exudation.

These defects typically cause metamorphopsia (distortion) which is detected clinically by Amsler grid testing. An Amsler grid consists of a chart with small squares. When choroidal neovascularization is manifested as fluid accumulation, hemorrhage, and/or lipid exudation the vision is distorted and the lines making up the squares of the grid become blurred and/or wavy.

Choroidal neovascularization occurs by vessels from the choroidal membrane growing through Bruch's membrane into the subretinal pigment epithelial or sub retinal space. This in itself can lead to severe visual loss, however, the retinal pigment epithelium or the neurosensory retina may also detach. Patients with pigment epithelial detachments may develop associated choroidal neovascular membranes. Even with no choroidal neovascular membranes present, 40% of patients with pigment epithelial detachments may continue to experience further loss of vision. Affected patients may exhibit metamorphopsia by Amsler grid testing.

Further consequences of exudative macular degeneration can include tearing of the retinal pigment epithelium and often development of a disciform scar with associated photoreceptor degeneration.

Both of the above-described forms of macular degeneration (non-exudative and exudative) usually proceed continuously toward irreversible loss of central vision. Ultimately, the retina is damaged by long-standing edema, underlying hemorrhage, and/or detachment. Following detachment, the retina may undergo fibrosis, metaplasia, elevation and scarring.

At present there is no one treatment that has proven to be truly effective therapy for treating or preventing the onset or progression of age-related macular degeneration.

There are several types of symptomatic treatment, however, that have been used with limited and isolated success, depending on the particular condition of the patient, to treat exudative (wet form) macular degeneration.

Laser photocoagulation therapy may benefit certain patients with macular degeneration. However, there are high recurrence rates for selected choroidal neovascular membranes which may initially respond to laser therapy. Vision loss may also result from the laser therapy.

Low dose radiation (teletherapy) has also been hypothesized as a possible treatment to induce regression of choroidal neovascularization.

Surgical removal of neovascular membranes is another possible treatment, but it is a highly specialized procedure and reportedly has not had promising results to date.

Interferon-$\alpha$ is a cytokine that is recognized for its ability to inhibit endothelial cell migration and proliferation in vitro, leukocyte induced androgenesis in animals, and life threatening hemangiomas in children. Interferon-$\alpha$ has been proposed as a possible drug therapy to inhibit the development of neovascular membranes and thereby decrease foveal destruction and related visual loss. The benefit of interferon-$\alpha$ therapy, however, is controversial. Even when reported as successful, the benefits of interferon-$\alpha$ therapy are extremely variable among different individuals and the typically high dose therapy is often associated with negative side effects.

There is presently no effective treatment for non-exudative (dry form) macular degeneration. Management of non-exudative macular degeneration is limited to early diagnosis and careful follow-up to determine if the patient develops choroidal neovascularization. Protection against exposure to ultraviolet light and prescribed dosages of anti-oxidant vitamins (e.g., vitamin A, $\beta$-carotene, lutein, zeaxanthin, vitamin C and vitamin E) and zinc may also be of some benefit, but as yet these treatments remain unproven. Additionally, the use of zinc has shown appreciable negative side effects including effects on heart disease and induction of copper deficiency anemia.

A method of treatment which effectively treats or prevents the onset or progression of this debilitating ocular disorder would be of considerable benefit. An effective method of treatment is especially needed to control the dry form of macular degeneration which afflicts 90% of the patients. Additionally, it has been estimated that most of the 1 million people identified as visually handicapped in Britain have macular degeneration and more than 10 million cases of the disease now exist in the U.S. Other studies suggest that 10% of the United States population between ages 65 to 74 and 30% of the population exceeding 75 years of age develop signs of macular degeneration in one form or the other.

SUMMARY OF THE INVENTION

One object of the present invention is to provide an effective method of treating or preventing the onset or progression of exudative and non-exudative macular degeneration, particularly the dry form (non-exudative) of the disease for which there has been little effective treatment other than the limited benefit of anti-oxidant vitamins.

Another object of the present invention is to provide a method which is useful as a synergistic treatment, for example, in conjunction with other treatments such as anti-oxidant and/or anti-inflammatory therapy.

A further object of the present invention is to provide a method of treatment to augment the currently available symptomatic treatments for macular degeneration, including: mechanical low vision aids (e.g., magnifiers or high-power glasses), acupuncture, laser photocoagulation therapy, and low dose radiation (teletherapy).

The present invention may also be used as a method of treatment for preventing the onset of macular degeneration induced by exposure to sunlight or for affecting other related conditions induced by exposure to sunlight.

These and other objects of the present invention are achieved by providing a method of treatment that increases intracellular levels of glutathione (GSH) in the human body.

The invention is based on the discovery that GSH is important in the treatment of macular degeneration and that by increasing the amount of intracellular GSH in the body, macular degeneration can be effectively treated and even prevented. To this end, the invention provides a method for treating macular degeneration by administration of an effective amount of a GSH enhancing agent to a human in need of such treatment. Preferably, the GSH enhancing agent is a non-toxic water-soluble cysteine derivative, most advantageously N-acetylcysteine, although other such agents may also be used.

Without intending to be limited to any theoretical explanation, it appears that N-acetylcysteine or like cysteine derivatives form cysteine in situ. The amino acid cysteine appears to be critical to GSH synthesis. Therefore, by controlling cysteine availability, for example, by increasing exogenous cysteine whenever cysteine synthesis is limited or whenever there is an increased need for GSH protection against toxic compounds, intracellular levels of GSH can be controlled.

GSH is a tripeptide composed of the three L-amino acids glutamic acid, glycine, and cysteine. GSH is synthesized intracellulary and is abundant or present in nearly all mammalian cells. Several of the many important biological functions that GSH serves are protection of the liver from ethanol, lymphoid cells from radiation, and the lungs against oxygen toxicity. Additionally, GSH is helpful in decreasing the toxicity of anti-cancer therapy and acetaminophen overdose, and increased GSH levels may even reduce immune incompetence associated with HIV infection.

Most importantly, GSH maintains sulfhydryl groups and protects cells against toxic compounds, particularly oxygen free radicals. Because GSH levels in cells are depleted by the increased presence of oxygen radicals, oxidative stress is another indicator of the need for a treatment which increases intracellular GSH levels. Since it is likely that oxidative stress occurs in patients that suffer from macular degeneration, enhancing the amount of GSH in the body should facilitate the treatment of macular degeneration.

In any case, and whatever the explanation may be, the discovery on which the invention is based is that enhancing GSH content provides a useful and effective way of treating macular degeneration.

DETAILED DESCRIPTION OF THE PREFERRED EMBODIMENTS

The method of treatment according to the present invention can be carried out in various ways each of which is aimed to increase the intracellular levels of GSH in patients suffering from different stages and forms of macular degeneration.

In a preferred embodiment, the intracellular levels of GSH are increased by periodically administering to the patient a dosage of a cysteine-supplying derivative, preferably N-acetylcysteine (NAC) or its equivalent. NAC is a known mucolytic agent. It is the N-acetyl derivative (HS—$CH_2$—CH—COOH—NH—$COCH_3$) of the naturally occurring amino acid, L-cysteine. NAC can be administered in any convenient manner, e.g. orally, intramuscularly, intravenously, or by aerosolization at doses ranging from 100 to 5600 milligrams daily. NAC is more soluble than cysteine in water and is less easily oxidized than cysteine. Hence, it is preferred to use NAC or an equivalent cysteine derivative rather than cysteine itself. It is believed, however, that once administered, it is cysteine, as noted earlier, which functions to increase GHS levels, and consequently, to treat or prevent tissue damage such as that observed in macular degeneration.

As indicated earlier, it is not fully understood how cysteine or its derivatives function to accomplish the intended treatment. However, it appears that the possible protective mechanisms offered by N-acetylcysteine (NAC) include: scavenging (inactivation of) oxygen radicals (e.g. $H_2O_2$, HOCl or ●OH) directly; inhibiting NFkB nuclear factor activation, which is a known link between viral infection and activation of oxidative processes; decreasing oxidant-induced lipid peroxidation and oxidant-induced inactivation of anti-proteases; and increasing blood flow, perhaps as a consequence of a potentiating action with nitric oxide.

NAC is a particularly desirable compound for use according to the invention as it is currently used clinically to treat patients with, for example, chronic bronchitis, acetaminophen overdose, and mustard gas exposure. NAC is also being tested as a treatment for ARDS, AIDS, ALS, and other conditions. NAC has been used safely for many years. For example, an oral dose of 600 mg tid is well tolerated for long periods of time in patients with chronic bronchitis and emphysema. Radiolabelled NAC is rapidly absorbed in humans one hour after administration and then distributed extensively. The mean plasma half-life of NAC is about 1.35 hours and approximately 22% of the dose is excreted in the urine after 24 hours. NAC appears to bind to protein and undergo some metabolism. Adverse effects following NAC treatment are rare but can include nausea, vomiting, pyrosis, dyspepsia, and very rarely, urticaria. These possible side effects can, however, generally be moderated to enable the treatment contemplated herein.

NAC is also advantageous for the present treatment of macular degeneration because it appears to augment antioxidant defense mechanisms by enhancing glutathione redox cycle activity. Specifically, NAC enables cysteine to penetrate cells. Increasing intracellular cysteine levels increases production of intracellular GSH which facilitates glutathione redox cycle activity (GSH$\leftrightarrows$GSSG). The effect of increased glutathione redox cycle activity is the continued detoxification of hydrogen peroxide ($H_2O_2$) and related hydroperoxides (e.g., hypochlorous acid and hydroxyl radicals). Hydrogen peroxide and hydrogen peroxide derived products are directly toxic to key cellular molecules (e.g., lipids, DNA, and proteins), and can accelerate inflammation. By increasing intracellular GSH levels, NAC treatment may reduce the toxic levels of intracellular hydrogen peroxide and related hydroperoxides that often relate to ocular tissue damage, specifically macular degeneration.

Another aspect of the invention is that intracellular GSH levels decline with age, and as a consequence, decreased GSH levels may enhance oxidative stress which contributes to ocular tissue damage. With the claimed method of treatment, NAC can be useful to prevent or reverse the ocular dysfunctions typical of elderly patients that would otherwise develop with macular degeneration.

Advantageously, the NAC is administered in the range of about 400–600 milligrams daily, preferably about 250 milligrams. This may be done orally, for example, twice a day, although the dose, frequency and form of administration may be varied depending on other factors.

In a variation of the invention, intracellular levels of GSH are increased by periodically administering to the patient a dosage of L-2-oxothiazolidine-4-carboxylate (OTC). OTC, or procysteine as it is commonly known, is effectively transported into cells where it is converted by the action of 5-oxoprolinase into L-cysteine. By mechanisms similar to those described above with respect to NAC, OTC can indirectly affect increased levels of GSH and thereby augment anti-oxidant defense mechanisms by enhancing glutathione redox cycle activity. OTC has been shown to be effectively transported into mouse and rat brains as evidenced by increased brain cystsine levels in the mouse and rat following OTC administration. The dosage of OTC used for present purposes, and the mode of administration are generally similar to those given above for NAC.

In another variation of the invention, intracellular levels of GSH are increased by periodically administering to the patient a dosage of mercaptopropionylglycine (MPG). MPG increases GSH levels by decreasing oxidative damage both in vivo and in vitro (i.e., MPG-reduced myocardial infract size following ischemia-reperfusion). Free radical scavenging has been postulated as a mechanism for the protective effect of MPG. When measured by pulse radiolysis in vitro, MPG has been shown to scavenge OH (hydroxyl radicals) at a rate constant of approximately $10^9 M^{-1} s^{-1}$. Experimental pretreatment with MPG has also been shown to increase free sulfhydryl (GSH) content in control animals and maintain normal free sulfhydryl levels in animals subjected to ischemia-reperfusion. Although the protective mechanism(s) by which MPG functions for present purposes is not known, there are several possible explanations. Thus, for example, GSH levels in cell tissue might be increased or maintained by MPG-induced glutathione synthesis and/or MPG-induced release of protein bound GSH. An alternative possibility is that GSH is spared by MPG. A further possibility is that MPG might act as a sulfhydryl radioprotector. In any case, the MPG appears to function as a GSH enhancing agent useful for present purposes.

The amount of MPG which is used and the mode of administration can also be varied, as in the case of NAC and OTC.

A unique aspect of the invention utilizing NAC, OTC, or MPG alone, or in a combination of two or more, or in conjunction with one or more anti-oxidant, anti-inflammatory, or current symptomatic treatments, is that direct treatment with GSH or cysteine would not be beneficial. An apparent reason for this is that neither unacetylated cysteine, nor GSH appear to penetrate cells by themselves. Moreover, cysteine itself may be toxic if it is oxidized extracellularly. Likewise, other anti-oxidants, for example antioxidant vitamins such as vitamin A, lutein, zeaxanthin, vitamin E, β-carotene, or vitamin C, may not be as effective because they also do not penetrate cells easily.

Macular degeneration can also occur in localized areas which are not recognized by routine examination until severe and often permanent eye destruction occurs. An additional advantage of the claimed method of treatment is that this problem can be overcome with a nontoxic treatment, such as NAC, OTC, or MPG, which can be used proactively to prevent the development of forms of macular degeneration which could not otherwise be detected earlier. A further advantage of the claimed method of treatment is that GSH enhancing agents, namely NAC, OTC, or MPG, can be administered locally through a variety of delivery systems including eye drops, liposomes or direct injection (intravitreal).

Broadly speaking, therefore, the invention contemplates using any agent which can enhance intracellular GSH levels to treat or prevent the onset or progression of macular degeneration. Preferably, NAC, OTC and/or MPG are used for this purpose but it will be appreciated that other GSH enhancing agents may also be useful.

The invention is further illustrated by the following nonrestrictive example:

EXAMPLE

A 78 year old white male was originally examined on Day One. At that time, the patient's best corrected visual acuity was 20/20-2 in the right eye (OD) and 20/50-1 in the left eye (OS). The patient complained of decreasing vision, including decreased color perception. The patient exhibited metamorphopsia in his left eye encompassing an area included in 71 squares on the standard Amsler grid. Similar Amsler grid testing disclosed no metamorphopsia in the patent's right eye (OD). The patient had been taking ocuvite anti-oxidant vitamins for many years. He continued to take these vitamins during the evaluation referred to herein.

About 2 months later, the patient began low dose interferon-α therapy, administered the first three days of each month, for treatment of an elevated prostate specific antigen. The dose was less than the usual high dose interferon-α therapy that has been tried as a possible treatment of choroidal neovascularization exudative (wet form) macular degeneration.

The following month, Amsler grid testing demonstrated increased metamorphopsia in the patient's left eye encompassing all or a portion of 87 squares. The patient felt that he might be developing further decreased vision and metamorphopsia in his right eye (OD). At this time, the patient's visual acuity in both eyes was unchanged. Fluorescein angiogram fundus photographs revealed numerous drusen in the patient's right eye and drusen with an associated pigment epithelial detachment in the patient's left eye. There was no indication at this time of a definite choroidal neovascular membrane in the left eye.

About 3 months later, the patient began periodic administration of N-acetylcysteine (NAC), 250 mgs orally, twice a day.

The patient's visual acuity was determined around 5 months later, to be 20/20-2 in the right eye (OD) and 20/60-1 in the left eye (OS). The patient had developed a new macular hemorrhage in the left eye which indicated the development of a choroidal neovascular membrane. Fundus studies revealed diffuse drusen in the patient's right eye and drusen, pigment epithelial detachment, and subretinal hemorrhage in the patient's left eye. There also was some evidence of a choroidal neovascular membrane associated with the pigment epithelial detachment in the left eye. The patient was carefully evaluated and it was felt that neither laser treatment, nor high dose interferon-α therapy would help the patient's left eye.

A month or so later, the area of subretinal hemorrhage had resolved in the patient's left eye.

Repeat fluorescein angiogram fundus photographs about 4 months later demonstrated a decrease in the number and size of drusen in the patient's right eye compared to photographs of the same right eye exactly one year before. Photographs of the retina of the patient's left eye demonstrated a decrease in the number and size of drusen in the left eye as well as hemorrhage resolution. The patient exhibited some pigmentary changes in the left eye.

In September of 1994, the patient's best corrected visual acuity was determined to be 20/20-2 in the right eye (OD) and 20/60-1+1 in the left eye (OS). The patient subjectively reported that his color perception had dramatically improved, especially in the left eye. Amsler grid testing showed that metamorphopsia had decreased to an area encompassing 41 grid squares. The patient felt that his visual acuity had improved dramatically since beginning treatment with NAC.

Treatment of the patient continued using NAC, anti-oxidant vitamins, and low dose interferon-α therapy.

Figure 1:
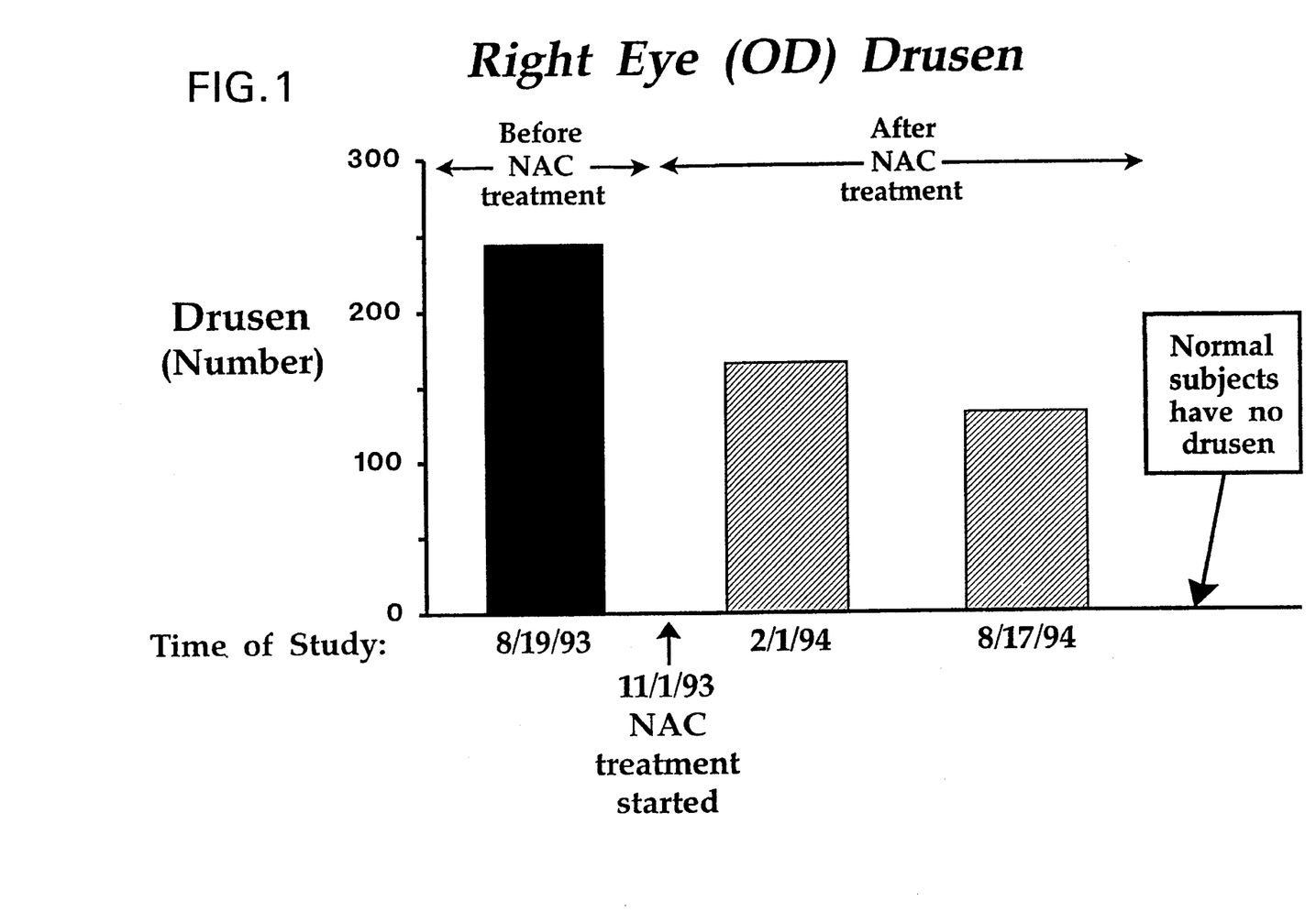
FIG. 1 is a graph showing the change in measured right eye (OD) drusen as a function of time and length of N-acetylcysteine (NAC) treatment according to the invention.
Figure 2:
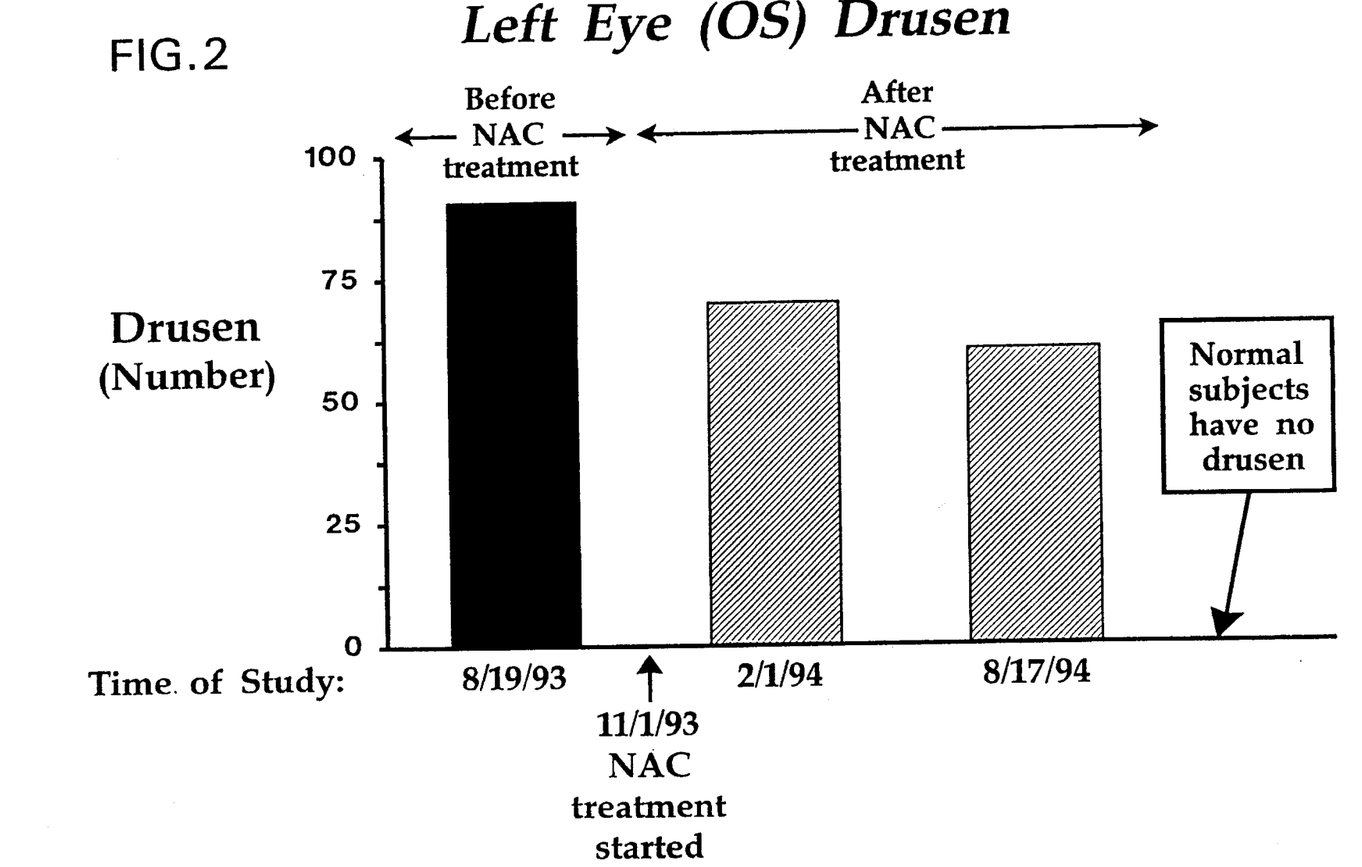
FIG. 2 is a graph showing the change in the measured left eye (OS) drusen as a function of time and length of NAC treatment.
Figure 3:
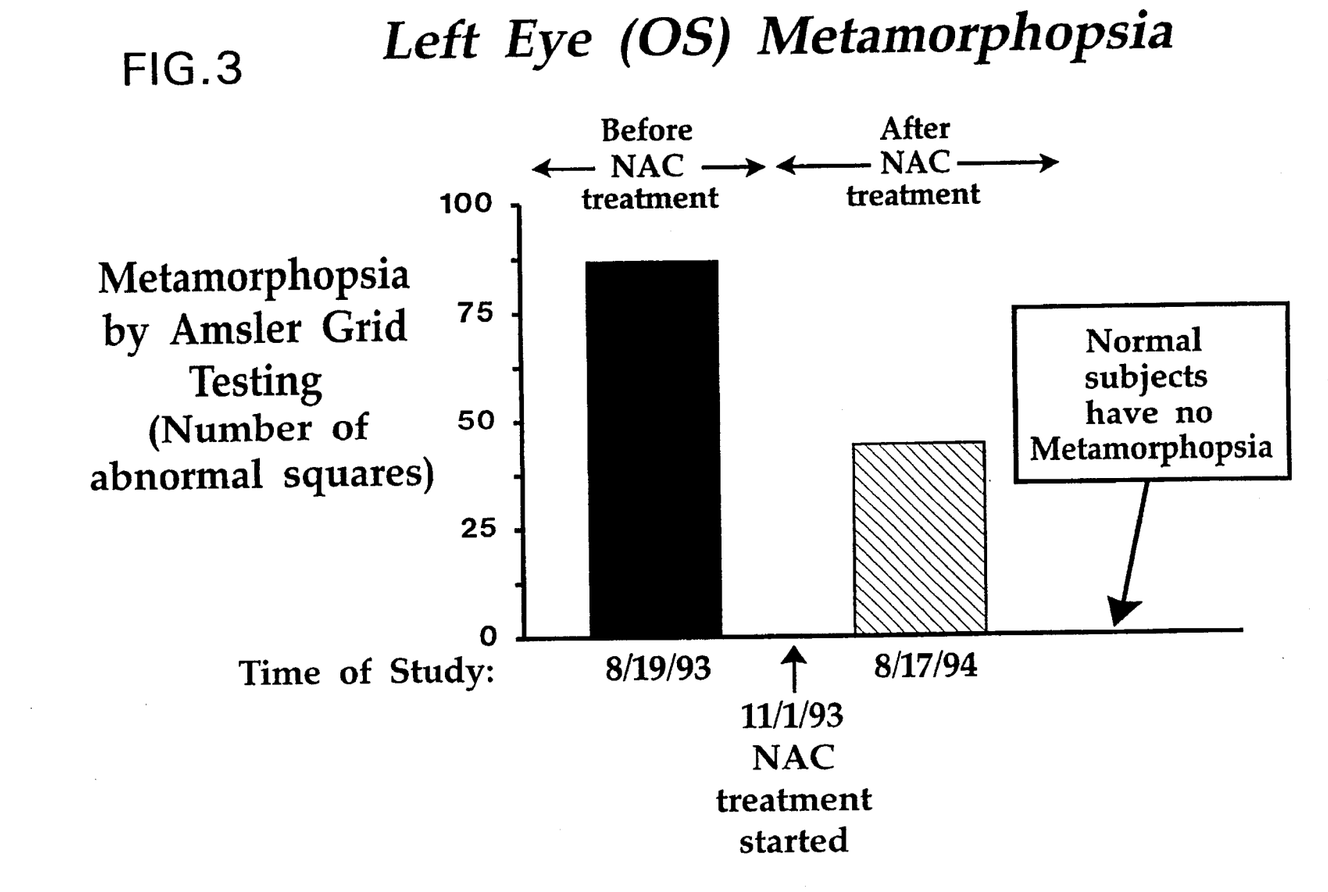
FIG. 3 is a graph showing the change in the left eye (OS) metamorphopsia measured by Amsler grid testing as a function of time and length of NAC treatment according to the invention.

The findings from the case history example given above are as follows:

1. Subjective visual improvement. The patient reported that his deteriorating vision had improved remarkably since beginning treatment with NAC. The patient was also keenly aware of an increase in color perception following the initiation of NAC therapy;

2. Objective visual improvement. The patient's Snellen visual acuity has not changed since beginning treatment with NAC;

3. Retinal photographic assessment of macular degeneration. Before treatment with NAC was begun, evaluation of the patient's right eye revealed many drusen formations. By comparison, approximately three months after the NAC treatment was initiated, the number of drusen had decreased substantially and, approximately nine months after the NAC treatment was initiated, there was an additional decrease in the number of drusen (FIG. 1). NAC treatment similarly decreased the number of drusen in the patient's left eye over the course of the year (FIG. 2);

4. Amsler grid testing. Amsler grid testing of the patient's left eye after about nine months of NAC treatment, showed dramatic improvement in metamorphopsia (i.e. a decreased number of abnormally seen grid squares) from the year before following the beginning of NAC treatment (FIG. 3).

It will be appreciated that various modifications may be made in the invention described herein. Accordingly, the scope of the invention is defined in the following claims.

What is claimed is:

1. A method for the treatment of macular degeneration in a patient in need of such treatment which comprises administering to said patient an effective amount of a glutathione enhancing agent to increase intracellular levels of glutathione in the patient.

2. The method of treatment according to claim 1, which comprises periodically administering a dosage of glutathione enhancing agent whereby intracellular levels of glutathione are increased, the glutathione enhancing agent being administered alone or in conjunction with at least one anti-oxidant, or at least one anti-inflammatory therapy, or a combination thereof.

3. The method of treatment according to claim 1, wherein the glutathione enhancing agent is N-acetylcysteine.

4. The method of treatment according to claim 1, wherein the glutathione enhancing agent is L-2-oxothiazolidine-4-carboxylate.

5. The method of treatment according to claim 1, wherein the glutathione enhancing agent is mercaptopropionylglycine.

6. The method of treatment according to claim 2, wherein the anti-oxidant is a vitamin selected from the group consisting of ascorbic acid (Vitamin C), α-tocopherol (Vitamin E), β-carotene, retinol (vitamin A), lutein, and zeaxanthin.

7. The method of treatment according to claim 2, wherein the anti-inflammatory therapy is interferon-α.

8. The method of treatment according to claim 2, wherein the dosage of glutathione enhancing agent is administered orally or by a delivery system selected from the group consisting of eye drops, liposomes, and direct intravitreal injection.

9. The method of treatment according to claim 3, wherein the dosage of N-acetylcysteine is in the range of about 400 to about 600 milligrams daily.

10. The method of treatment according to claim 3, wherein the dosage of N-acetylcysteine is about 250 milligrams administered orally twice per day.

11. A method for preventing the onset or progression of exudative and non-exudative macular degeneration which comprises, periodically administering a dosage of glutathione enhancing agent whereby intracellular levels of glutathione are increased, the glutathione enhancing agent being administered alone or in conjunction with at least one anti-oxidant, or at least one anti-inflammatory therapy or a combination thereof.

12. A method for improving symptomatic treatments of exudative and non-exudative macular degeneration which comprises;

periodically administering a dosage of a glutathione enhancing agent whereby intracellular levels of glutathione are increased, the glutathione enhancing agent being administered alone or in conjunction with at least one anti-oxidant, or at least one anti-inflammatory therapy or a combination thereof, and in addition to at least one symptomatic treatment.

13. The method of treatment according to claim 12, wherein the at least one method of symptomatic treatment is selected from the group consisting of mechanical low vision aids, acupuncture, laser photocoagulation therapy, and low dose radiation (teletherapy).

14. A method according to claim 1, wherein the glutathione enhancing agent is a thiol compound or a thiol-yielding compound that can penetrate cells.

* * * * *

(12) REEXAMINATION CERTIFICATE (4759th)
United States Patent
Repine et al.

(10) Number: US 5,596,011 C1
(45) Certificate Issued: Apr. 8, 2003

(54) METHOD FOR THE TREATMENT OF MACULAR DEGENERATION

(75) Inventors: Karen M. Repine, Englewood, CO (US); John E. Repine, Englewood, CO (US)

(73) Assignee: Cherry Hills Farmaceutical, LLC, Cherry Hills, CO (US)

Reexamination Request:
No. 90/005,398, Jun. 17, 1999

Reexamination Certificate for:
Patent No.: 5,596,011
Issued: Jan. 21, 1997
Appl. No.: 08/418,645
Filed: Apr. 6, 1995

(51) Int. Cl.$^7$ .................... A61K 31/425; A61K 31/195; A61K 31/13
(52) U.S. Cl. .................... 514/369; 514/562; 514/665; 514/912
(58) Field of Search .................... 514/369, 562, 514/665, 912

(56) References Cited

U.S. PATENT DOCUMENTS

| | | | |
|---|---|---|---|
| 5,075,116 A | 12/1991 | La Haye et al. | |
| 5,156,852 A | 10/1992 | La Haye et al. | |
| 5,208,249 A | 5/1993 | Rowe et al. | |
| 5,310,764 A | 5/1994 | Baranowitz et al. | |
| 5,632,984 A | 5/1997 | Wong et al. | |

OTHER PUBLICATIONS

J.C. Seagrave et al., "Zinc effects on glutathione metabolism relationship to zinc–induced protection from alkylating agents," Biochemical Pharmacology, vol. 32, No. 20, (1983) pp. 3017–3021.

G.J. Handelman et al., "Carotenoids in the Human macula and whole retina," Investigative Opthalmology & Visual Science, vol. 29, No. 6, Jun. 1988, pp. 850–855.

W. Schalch "Carotenoids in the retina—A review of their possible role in preventing or limiting damage caused by light and oxygen," Free Radicals and Aging, vol. 62, 1992, pp. 280–298.

J.M. Seddon et al., "Dietary carotenoids, vitamins A, C, and E, and advanced age–related macular degeneration," JAMA the Journal of the American Medical Association, vol. 272, No. 18, Nov. 1994, pp. 1413–1420.

S. H. Sarks, John P. Sarks, "Age–Related Macular Degeneration: Atrophic Form, vol. Two, Macular Disease," Chapter 64, 1989, pp. 149–173.

S. West et al., "Are Antioxidants or Supplements Protective for Age–Related Macular Degeneration?," Archives of Ophthalmology, Feb. 1994, pp. 222–227.

M.M.E. Bridgeman et al., "Cysteine and Glutathione Concentrations in Plasma and Bronchoalveolar Lavage Fluid after Treatment with N–Acetylcysteine," Dept. of Biochemistry, U. of Edinburgh, Medical School, pp. 39–42.

M.M.E. Bridgeman et al., "Effect of N–Acetyl Cysteine on the Concentrations of Thiols in Plasma, Bronchoalveolar Lavage Fluid, and Lung Tissue," Dept. of Biochemistry, U. of Edinburgh Med. School, 1994, pp. 670–675.

B. de Quay et al., "Glutathione Depletion in HIV–Infected Patients: Role of Cysteine Deficiency and Effect of Oral N–Acetylcysteine," Current Science Ltd., 1992, pp. 875–876.

Wayne E. Fung, "Interferon Alpha 2a for Treatment of Age–Related Macular Degeneration, American Journal of Ophthalmology," Sep. 1991, pp. 349–350.

W. de Backer, "Inflammatory Mediators in Acute Lung Injury and Copd: Effects of N–Acetylcysteine," Pulmo script, Sep. 1994.

G. R. Bernard, "N–Acetylcysteine in Experimental and Clinical Acute Lung Injury," The American Journal of Medicine, Sep. 1991.

O.I. Aruoma et al., "The Antioxidant Action of N–Acetylcysteine: Its Reaction with Hydrogen Peroxide, Hydroxyl Radical, Superoxide, and Hypochlorous Acid," Free Radical Biology & Medicine, 1989, pp. 593–597.

I.H. Chisholm, "The Prospects for New Treatments in Age–Related Macular Degeneration," British Journal of Ophthalmology, 1993.

P. Ko et al., "Understanding Macular Degeneration," Hospital Medicine, Sep. 1994, pp. 47–55.

J.M. Seddon et al., "Vitamins, Minerals, and Macular Degeneration," Archives of Ophthalmology, 1994, pp. 176–179.

*Primary Examiner*—Zohreh Fay (57) ABSTRACT

Macular degeneration is an age-related eye disease for which there is no known treatment to date that has been shown to be effective at treating or preventing the onset or progression of the disease. Current treatment of non-exudative (dry form) macular degeneration is limited to early diagnosis and careful followup, while symptomatic treatment of exudative (wet form) macular degeneration includes laser photocoagulation therapy, surgery, low dose radiation (teletherapy), and anti-oxidant or anti-inflammatory therapies. The present invention relates to a new method for treating or preventing the onset or progression of macular degeneration, comprising periodic administration of a glutathione (GSH) enhancing agent alone or in conjunction with at least one of an anti-oxidant or an anti-inflammatory therapy, and possibly in addition to one or more of the symptomatic treatments mentioned above.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 11–14 are cancelled.

Claim 1 is determined to be patentable as amended.

Claims 2–10, dependent on an amended claim, are determined to be patentable.

New claim 15 is added and determined to be patentable.

1. A method for the treatment of macular degeneration in a patient in need of such treatment which comprises administering to said patient an effective amount of a glutathione enhancing agent to increase intracellular levels of glutathione in the patient, *said glutathione enhancing agent being selected from the group consisting of N-acetylcysteine, L-2-oxothiozolidone-4-carboxylate and mercaptopropionyl glycine.*

*15. The method of claim 1, wherein administering to said patient said effective amount of said glutathione enhancing agent decreases the number and size of drusen in the eye of said patient.*

\* \* \* \* \*